(12) United States Patent
Yin et al.

(10) Patent No.: US 12,133,887 B2
(45) Date of Patent: Nov. 5, 2024

(54) **CHEMICAL SYNTHESIS OF OLIGOSACCHARIDES OF *PSEUDOMONAS AERUGINOSA* SEROTYPE O11 O-ANTIGEN**

(71) Applicant: Jiangnan University, Wuxi (CN)

(72) Inventors: Jian Yin, Wuxi (CN); Jing Hu, Wuxi (CN); Zhonghua Liu, Wuxi (CN); Chunjun Qin, Wuxi (CN)

(73) Assignee: Jiangnan University, Wuxi (CN)

( * ) Notice: Subject to any disclaimer, the term of this patent is extended or adjusted under 35 U.S.C. 154(b) by 1065 days.

(21) Appl. No.: 17/017,896

(22) Filed: Sep. 11, 2020

(65) Prior Publication Data

US 2020/0405840 A1    Dec. 31, 2020

Related U.S. Application Data

(63) Continuation of application No. PCT/CN2019/119584, filed on Nov. 20, 2019.

(30) Foreign Application Priority Data

Dec. 18, 2018  (CN) .......................... 201811551666.0

(51) Int. Cl.
| | |
|---|---|
| *A61K 39/104* | (2006.01) |
| *A61K 31/738* | (2006.01) |
| *C07H 1/00* | (2006.01) |
| *C07H 3/06* | (2006.01) |
| *A61K 39/00* | (2006.01) |

(52) U.S. Cl.
CPC .......... *A61K 39/104* (2013.01); *A61K 31/738* (2013.01); *C07H 1/00* (2013.01); *C07H 3/06* (2013.01); *A61K 39/00* (2013.01)

(58) Field of Classification Search
CPC ...... A61K 39/104; A61K 31/738; C07H 1/00; C07H 15/04; C07H 3/06
USPC .......................................................... 514/23
See application file for complete search history.

(56) References Cited

FOREIGN PATENT DOCUMENTS

| | | | |
|---|---|---|---|
| CN | 107709343 A | 2/2018 | |
| CN | 108558961 A | * 9/2018 | ............. C07H 15/04 |
| CN | 109627270 A | 4/2019 | |

OTHER PUBLICATIONS

D'Ambra et al., Carbohydrate Research, 1994, 251, 127-144.*
Qin et al., Journal of the American Chemical Society, 2018, 140, 3120-3127.*
PCT/CN2019/119584 ISA210 ISR Mail Date Feb. 19, 2020.
D''Ambra, Anello J. ~ Analysis by the Reductive-cleavage Method of a Polysaccharide Containing 2-acetamido-2, 6-dideoxy-D and -L-galactopyranosyl Residues Carbohydrate Research Jan. 3, 1994, vol. 251 p. 128.
Qin, Chunjun , Total Synthesis of a Densely Functionalized Plesiomonas Shigelloides Serotype 51 Aminoglycoside, Trisaccharide Antigen Journal of the American Chemical Society, Jan. 29, 2018, vol. 8, Issue 140 p. 3122.

* cited by examiner

*Primary Examiner* — Ganapathy Krishnan
(74) *Attorney, Agent, or Firm* — IPRO, PLLC; Na Xu (57) ABSTRACT

The disclosure discloses a chemical synthesis method of oligosaccharides of a *Pseudomonas aeruginosa* serotype O11 O-antigen, and belongs to the field of chemistry. The disclosure includes constructing an O-antigen trisaccharide by using a D-glucose building block, an L-fucosamine building block and a D-fucosamine building block; wherein the D-glucose building block or the L-fucosamine building block is linked with the D-fucosamine building block through a 1,2-α-cis-glycosidic bond, the D-glucose building block is linked with the L-fucosamine building block through a 1,2-β-trans-glycosidic bond, and the construction of the 1,2-α-cis-glycosidic bond is conducted in a mixed solvent; and the mixed solvent includes two or more of dichloromethane, diethyl ether and thiophene. According to the method of the disclosure, D-mannose is taken as a raw material, D-fucose is obtained simply, conveniently and efficiently, depending on suitable mixed solvents, the uniform construction of a cis-glycosidic bond of the D-fucose is achieved, the stereoselectivity can be up to 100%, and a very good application prospect in the aspects of the development of novel medicines and vaccines against *Pseudomonas aeruginosa* and the like is achieved.

4 Claims, 8 Drawing Sheets

FIG. 8

CHEMICAL SYNTHESIS OF OLIGOSACCHARIDES OF *PSEUDOMONAS AERUGINOSA* SEROTYPE O11 O-ANTIGEN

TECHNICAL FIELD

The disclosure relates to a chemical synthesis method of oligosaccharides of a *Pseudomonas aeruginosa* serotype O11 O-antigen, and belongs to the field of chemistry.

BACKGROUND

*Pseudomonas aeruginosa* is a kind of aerobic and rod-shaped Gram-negative bacteria, which generally inhabits in the soil and water environment. In particular, the *Pseudomonas aeruginosa* is also a kind of opportunistic pathogens widely existing in the hospital environment, causing bacteremia, urinary tract infection, pneumonia and other diseases. The susceptible population of the *Pseudomonas aeruginosa* includes burn patients, patients in ICU, postoperative patients and patients with immune system defects such as cancer, diabetes and congenital cystic fibrosis. It was found by the study of the prevalence of the *Pseudomonas aeruginosa* in ventilator-associated pneumonia (VAP) and hospital acquired pneumonia (HAP) in mainland China that in the VAP, the *Pseudomonas aeruginosa* accounted for 19.4% (17.6-21.2% of 95% confidence interval (CI)) of all isolated strains, and the proportion in the HAP was relatively similar and was 17.8% (14.6-21.6% of 95% CI). In addition, the study further found that the *Pseudomonas aeruginosa* isolated from the VAP had high resistance to gentamicin (51.1%, 37.7-64.4% of 95% CI) and amikacin (22.5%, 14.3-33.6% of 95% CI), while the *Pseudomonas aeruginosa* isolated from the HAP had high resistance to amikacin (22.2%, (13.8-33.6% of 95% CI)) and cefoperazone (50.0%, (30.2-69.8% of 95% CI)).

Globally, it was clinically found that the *Pseudomonas aeruginosa* has resistance to antibiotics including polymyxin, fluoroquinolones, carbapenems and the like. In 2016, the World Health Organization listed the *Pseudomonas aeruginosa* as one of pathogens for which novel antibiotics or vaccines are in the most urgent need to be studied and developed. Up to now, there is no vaccine for the pathogens on the market. The vaccine research on the *Pseudomonas aeruginosa* began in the 1980s. The research fields focus on lipopolysaccharide, glycol-protein conjugate, flagella, inactivated or attenuated whole bacteria and DNA sequence of the pathogens. The lipopolysaccharide of the *Pseudomonas aeruginosa* is composed of linking some unusual monosaccharides in human bodies and glycosidic bonds, which is an important virulence factor. There are 20 different serotype antigens in the *Pseudomonas aeruginosa* based on the linkage modes of the monosaccharides and glycosidic bonds. A serotype O11 antigen with a specific structure of [-3)-α-L-N-acetylfucosamine-(1-3)-β-D-N-acetylfucosamine-(1-2)-β-D-glucose-(1-]$_n$ is a long-chain antigen formed by linking trisaccharide repeat fragments end-by-end, and the specific number of repeat units n is controlled by genes of the antigen.

At present, all such structural compounds are extracted from the wild pathogens containing the lipopolysaccharide structure or genetic engineering bacteria coding the structure, and include a series of steps of construction and culture of LPS high-expression strains, degradation of protease K, carbolic acid thermal extraction, Tricine-SDS-polyacrylamide gel electronophoresis (PAGE) analysis, Western immunoblot detection and the like. In addition, the lipopolysaccharide obtained by a biological extraction method also has the problem of uneven chemical structure, and meanwhile further has the problem of safety, because the lipopolysaccharide directly extracted from bacteria is likely to be doped with other bacterial virulence factors, not only can it not provide immune protection to human bodies, but it will make the human bodies sick due to direct infection by bacterial virulence factors, which will cause serious side effects. In order to avoid such problems, we decided to use the chemical synthesis method to directly synthesize the lipopolysaccharide, so as to avoid the problem of uneven chemical structure and doping other unknown virulence factors, the synthesized lipopolysaccharide has a clear chemical structure, and it can be ensured that only this kind of capsular polysaccharide participates in the composition of the vaccine, without doping other substances.

However, in the process of complex oligosaccharide synthesis, the construction of the glycosidic bonds is the most basic and the most difficult and key problem in oligosaccharide synthesis, due to the diversity of a carbohydrate structure and the complexity of stereochemistry, different from organic compounds of other structures, the methodology of oligosaccharide synthesis is still immature and imperfect, which is considered as the only one in the field of organic chemistry which has many methods (dozens of methods), but has no universal method generally accepted. Because of the complex structure of saccharide modules and the low selectivity of a cis-glycosidic bond, it is difficult to synthesize and construct the structure, and at present, there is no report on the use of chemical synthesis methods to construct the compound, which restricts the research on the chemical synthesis method to dissolve the structure.

SUMMARY

In order to solve the above problems, the disclosure synthesizes O-antigen trisaccharide fragments of a *Pseudomonas aeruginosa* serotype O11 by three saccharide building block chemical methods, mainly including a glucose building block, an L-fucosamine building block, a D-fucosamine building block, a 1,2-α-cis-glycosidic bond and a 1,2-β-trans-glycosidic bond. Among them, the synthesis of D-fucosamine and the construction of the 1,2-α-cis-glycosidic bond are the key steps of the target trisaccharide. The disclosure develops a method for synthesizing the D-fucosamine from D-glucose, and successfully solves the stereoselectivity problem of constructing the 1,2-α-cis-glycosidic bond through the synergetic effect of a solvent effect, a temperature effect and an additive effect. The protected target trisaccharide is synthesized by using the three synthesized glycosyl building blocks, and finally the target trisaccharide obtained by removing protection is as shown in a formula 1. At the same time, a reducing end of the trisaccharide is assembled with a linker arm with an amino group to prepare for the next step of conjugated protein.

The first object of the disclosure is to provide a synthesis method of an O-antigen trisaccharide of a *Pseudomonas aeruginosa* serotype O11. The synthesis method includes constructing O-antigen trisaccharide by using a D-glucose building block, an L-fucosamine building block and a D-fucosamine building block; wherein the D-glucose building block or the L-fucosamine building block is linked with the D-fucosamine building block through a 1,2-α-cis-glycosidic bond, the D-glucose building block is linked with the L-fucosamine building block through a 1,2-β-trans-glycosidic bond, and the construction of the 1,2-α-cis-glycosidic bond is conducted in a mixed solvent; and the mixed solvent includes two or more of dichloromethane, diethyl ether and thiophene.

In one embodiment of the disclosure, a chemical structural formula of the D-glucose building block is as shown in a formula II, a chemical structural formula of the L-fucosamine building block is as shown in a formula III, and a chemical structural formula of the D-fucosamine building block is as shown in a formula IV, formula II

A formula III

B formula IV

C wherein linker includes —(CH$_2$)$_n$—N—Y$_1$Y$_2$, or O—(CH$_2$)$_n$—SY$_1$(Y$_2$), or O—(CH$_2$)$_n$—N$_3$, and n=1- 10; Y$_1$ is hydrogen (H) or benzyl (Bn); Y$_2$ is hydrogen (H) or benzyl methoxycarbonyl (Cbz); R$_1$ includes but is not limited to hydrogen (H), an ester group, acetyl (Ac), benzoyl (Bz), pivaloyl (Piv), chloracetyl (ClAc), levulinyl (Lev) and allyl carbonyl (Alloc); R$_2$, R$_3$ and R$_4$ are hydrogen (H) or an ester group and an ether group, and include but are not limited to acetyl (Ac), benzoyl (Bz), pivaloyl (Piv), chloracetyl (ClAc), levulinyl (Lev), allyl carbonyl (Alloc), benzyl (Bn), p-methoxybenzyl (pMBn), allyl (All), triphenylmethyl (Tr), monomethoxy triphenyl methyl (Mmt) and a silyl ether group; R$_5$ and R$_6$ include but are not limited to hydrogen (H), an ether group, benzyl (Bn), p-methoxybenzyl (pMBn), allyl (All), triphenylmethyl (Tr), monomethoxy triphenyl methyl (Mmt) and a silyl ether group; and R$_7$, R$_8$ R$_9$ and R$_{10}$ include hydrogen (H), nitrogen (N) or acetyl (Ac).

In one embodiment of the disclosure, the method includes synthesizing a disaccharide fragment by using the D-glucose building block and the L-fucosamine building block, wherein a chemical structural formula of the disaccharide fragment is as shown in a formula V, formula V

D

In one embodiment of the disclosure, the linkage of the 1,2-β-trans-glycosidic bond between the D-glucose building block and the L-fucosamine building block is conducted in the dichloromethane as a solvent under the promotion of TMSOTf.

In one embodiment of the disclosure, the method includes synthesizing a trisaccharide fragment by using the disaccharide fragment and the D-fucosamine building block, wherein a chemical structural formula of the trisaccharide fragment is as shown in a formula I, formula I wherein R is —(CH$_2$)$_n$—NH$_2$, or O—(CH$_2$)$_n$—SH; and n=1-10.

In one embodiment of the disclosure, the method includes pre-synthesizing a precursor of the O-antigen trisaccharide, and obtaining the O-antigen trisaccharide by reduction, wherein a chemical structural formula of the precursor of the O-antigen trisaccharide is as shown in the following general formula, formula VI

E wherein R is —(CH$_2$)$_n$—NH$_2$, or O—(CH$_2$)$_n$—SH; and n=1-10.

In one embodiment of the disclosure, a structure of an O-antigen trisaccharide compound is as follows:

In one embodiment of the disclosure, an end group of the D-glucose building block (formula II) is trichloroacetimidate, which is a leaving group, and the rest of substituent groups $R_n$ are shown in the formula II.

In one embodiment of the disclosure, a synthesis method of the D-glucose building block includes taking 1,2,3,4,6-penta-O-acetyl glucose as a starting raw material, removing the acetyl at position 1 by using dried N,N-dimethylformamide and hydrazine acetate so as to expose —OH, and obtaining the compound D-glucose building block by reacting the exposed —OH with trichloroacetonitrile ($Cl_3CN$).

In one embodiment of the disclosure, an end group of the L-fucosamine building block (formula III) is protected by allyl (All), and substituent groups $R_n$ at the rest of positions are shown in the formula III.

In one embodiment of the disclosure, the L-fucosamine building block is obtained by a process that allyl 2-deoxy-2 azido-L-fucoside is taken as a starting raw material, and the hydroxyl at position 4 is selectively protected under the action of dibutyltin oxide ($Bu_2SnO$) and 2-bromomethyl-naphthalene to obtain 4-Nap fucose; and then the remaining hydroxyl at position 3 is protected by the benzyl, and then the Nap group at position 4 is removed under the action of dichlorodicyanobenzoquinone to obtain a final saccharide building block B.

In one embodiment of the disclosure, an end group of the D-fucosamine building block is a linker, as shown in the formula IV.

In one embodiment of the disclosure, a synthesis method of the D-fucosamine building block uses glucose to construct D-fucosamine, and includes taking 3,4,6-tri-O-acetyl-D-glucal as a raw material, obtaining 1-selenophenyl-2 azido glucose through an azide and a selenium reagent, removing acetyl, then methylating 6-C, and finally obtaining a D-fucosamine compound.

In one embodiment of the disclosure, the synthesis method specifically includes taking the 3,4,6-tri-O-acetyl-D-glucal as the raw material, generating 1-selenophenyl-2 azido glucose with azidotrimethylsilane (TMS-$N_3$) and diphenyl disenenide ($Ph_2Se_2$) under the action of iodobenzene diacetate (PhI(OAc)$_2$), then removing acetyl under an alkaline condition, achieving 6-C methylation by adding 4-toluenesulfonyl chloride, and obtaining the D-fucosamine compound.

In one embodiment of the disclosure, the synthesis method further includes protecting 3,4-C of the D-fucosamine compound, then removing a Nap group of 4-C, protecting with the acetyl, hydrolyzing the selenophenyl at position 1 of the D-fucose by tetrabutylammonium bromide (NBS), making the fucose into glycosyl trichloroacetimidate with $Cl_3CN$ and DBU, then assembling an aminolink under the promotion of lewis acid, and finally removing the acetyl at position 3 of the D-fucose to obtain the D-fucosamine building block.

In one embodiment of the disclosure, a protective reagent of the 3-C includes methoxybenzyl chloride (PMBCl) and dibutyltin oxide ($Bu_2SnO$).

In one embodiment of the disclosure, a protective reagent of the 4-C includes the benzyl.

In one embodiment of the disclosure, the removal of the Nap group of the 4-C is achieved by DDQ.

In one embodiment of the disclosure, the lewis acid includes trimethylsilyl trifluoromethanesulfonate.

The second object of the disclosure is to provide an O-antigen trisaccharide of a *Pseudomonas aeruginosa* serotype O11 assembled with an aminolink, which is prepared by the above method;

a structure of the O-antigen trisaccharide of the *Pseudomonas aeruginosa* serotype O11 assembled with the aminolink is as follows:

formula VI wherein R is —(CH$_2$)$_n$—NH$_2$; and n=1-10.

The third object of the disclosure is to provide a preparation method of a glycol-protein conjugate, and the preparation method uses the O-antigen trisaccharide of the *Pseudomonas aeruginosa* serotype O11 assembled with the aminolink.

The fourth object of the disclosure is to provide the preparation method of the glycol-protein conjugate, the preparation method includes the O-antigen trisaccharide of the *Pseudomonas aeruginosa* serotype O11, and the preparation method of the O-antigen trisaccharide of the *Pseudomonas aeruginosa* serotype O11 is the above method.

The fifth object of the disclosure is to apply an O-antigen trisaccharide of a *Pseudomonas aeruginosa* serotype O11 assembled with an aminolink to development or preparation of *Pseudomonas aeruginosa* vaccines or medicines for diseases caused by *Pseudomonas aeruginosa* infection.

Beneficial Effects of the Disclosure

1. The disclosure is to synthesize the O-antigen trisaccharide fragment of the *Pseudomonas aeruginosa* serotype O11 by a chemical method. In the disclosure, a method for converting D-mannose to D-fucose is developed, which is simple, convenient and efficient, and except about 50% of 6-C methylation, the rest can be more than 80%; and then the obtained glycosyl building blocks are used for synthesizing the O-antigen trisaccharide fragment of the *Pseudomonas aeruginosa* serotype O11

2. The construction of a common glycosidic bond is to construct a 1,2-trans-glycosidic bond with high efficiency by using a neighboring group assisted by C-2 acyl of a saccharide ring, 2-acetyl is the most easily available and most effective protector in the saccharide chemical protection strategy, such as the construction of the trans glycosidic bond in the disclosure. However, for the 1,2-cis reaction, because the reaction method is not universal, each reaction condition has a great influence on the reaction, among them, there are reports of selective protection with large space steric hindrance protective groups at C-6 when designing the saccharide building blocks and the introduction of acyl at C-4 especially for galactose to form a mechanism similar to the long-range neighboring assistance, the synthesis method of the disclosure adopts a suitable mixed solvent to achieve the even construction of the cis glycosidic bond, and the stereoselectivity can reach 100%.

3. The disclosure successfully completes the preparation of O11 trisaccharide repeat units through the selection and optimization of protective groups and the strategy of glycosidization reaction. The O-antigen trisaccharide fragment of the *Pseudomonas aeruginosa* serotype O11 assembled with the aminolink which is synthesized by the disclosure can be linked with an antigen protein to prepare a glycoconjugate, which plays an important role in the development of vaccines for treatment and prevention of *Pseudomonas aeruginosa*.

DETAILED DESCRIPTION

The embodiments of the disclosure will be described in detail below in conjunction with examples, but those skilled in the art will understand that the following examples are only for illustrating the disclosure and should not be considered as limiting the scope of the disclosure. If the specific conditions are not specified in the Examples, the conventional conditions or the conditions recommended by the manufacturer are used, and if the reagents or instruments used are not specified by the manufacturer, they are all conventional products that are commercially available.

A calculation method of the yield of the disclosure is "product (mol)/reaction substrate (mol)*100%". The methods for identifying the structure of compounds in the disclosure are nuclear magnetic resonance spectrometry (400 M), high-resolution mass spectrometry, and polarimetry, and results are listed in specific synthesis of each compound.

Example 1

Figure 1:
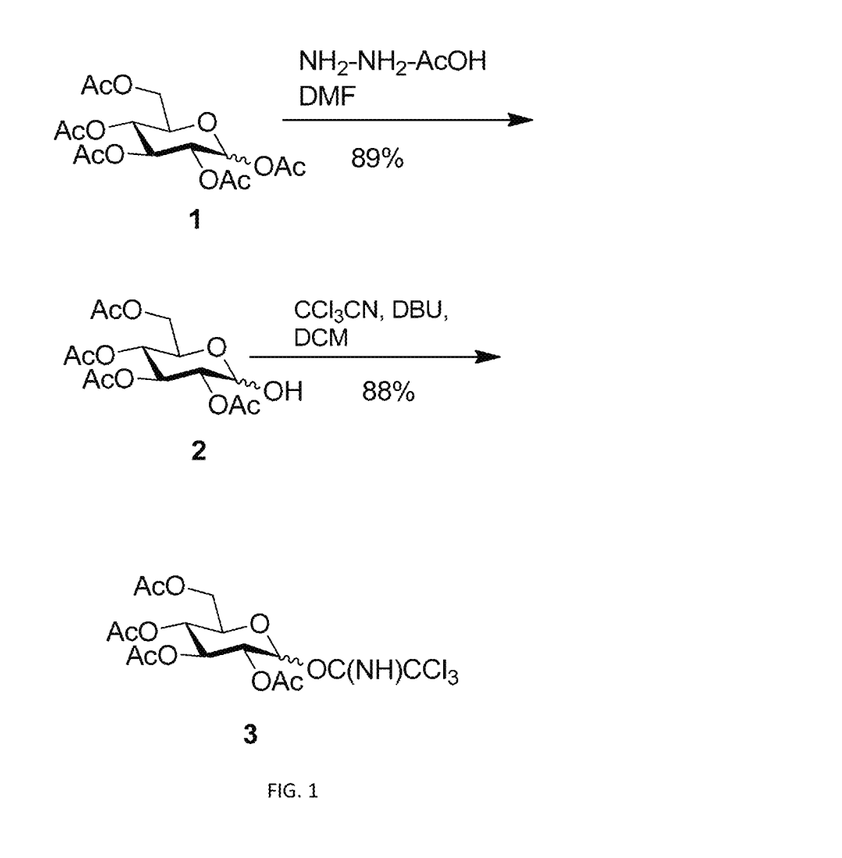
FIG. 1: a synthetic route map of a monosaccharide building block 3 (a D-glucose building block)

The synthesis of a saccharide building block 3 (a D-glucose building block) is as shown in FIG. 1:

As shown in FIG. 1, acetyl at position 1 is selectively hydrolyzed by hydrazine acetate ($NH_2$—$NH_2$—AcOH) in dried N,N-dimethylformamide with peracetyl glucose 1 as a starting raw material. Obtained 1-OH glucose 2 is then used to generate glucosyl trichloroacetimidate 3 in anhydrous dichloromethane by using trichloroacetonitrile ($Cl_3CN$) and 1,8-diazabicycloundec-7-ene (DBU).

Specific Test Operation and Steps:

Compound 2: the peracetyl glucose 1 (5.0 g, 12.8 mmol) is dissolved in anhydrous DMF (65 ml), and hydrazine acetate (1.45 g, 15.6 mmol) is added. The reaction is stirred at 40° C. for 6 h, and the disappearance of reactants is monitored by TLC. A reaction liquid is cooled to a room temperature and washed with a saturated NaCl solution, an organic phase is separated, dried with anhydrous $Na_2SO_4$ and purified by a silicagel column (petroleum ether/ethyl acetate, 2:1) after concentrating to obtain the compound 2 (3.9 g, 11.2 mmol). The identification data of the compound have been reported in related literature.

Compound 3: the compound 2 (1.1 g, 3.16 mmol) is dissolved in anhydrous DCM (30 ml) and cooled to 0° m, $Cl_3CN$ (3.2 ml, 31.6 mmol) and DBU (0.45 ml, 0.3 mmol) are sequentially added into a reaction liquid, the reaction is stirred in an ice bath for 4 h, and the disappearance of reaction raw materials is monitored by the TLC. The reaction liquid is recovered to the room temperature, and extracted by saturated $NaHCO_3$, an organic phase is separated, dried by anhydrous $Na_2SO_4$ and purified by the silicagel column (petroleum ether/ethyl acetate, 4:1) after concentrating to obtain the compound 3 (1.3 g, 2.8 mmol). The identification data of the compound have been reported in related literature.

Example 2

Figure 2:
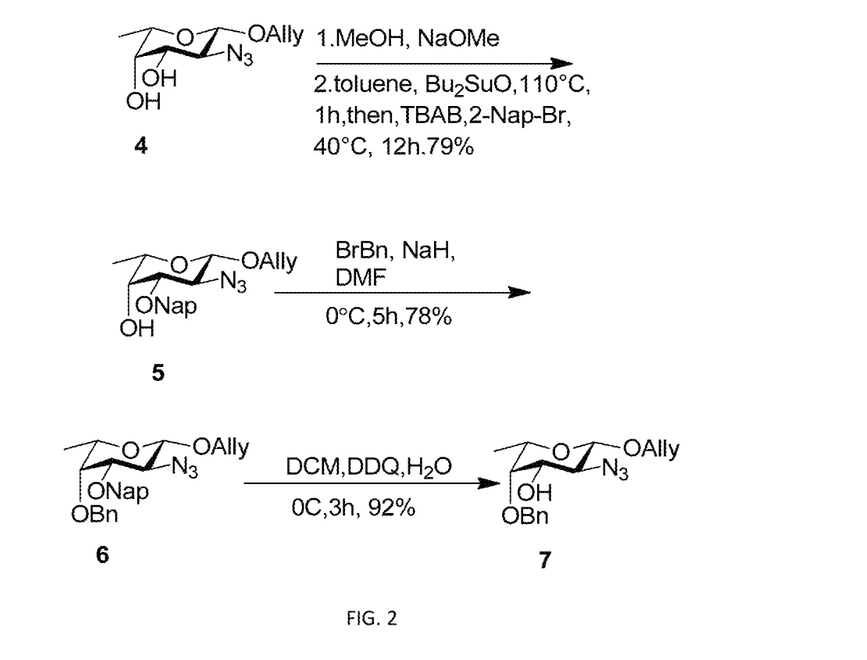
FIG. 2: a synthetic route map of a monosaccharide building block 7 (an L-fucosamine building block)

The synthesis route of a saccharide building block 7 (an L-fucosamine building block) is FIG. 2

As shown in FIG. 2, ally 2-deoxy-2 azido-L-fucoside 4 is taken as a starting raw material, acetyls at positions 3 and 4 are removed under the alkaline environment containing sodium methoxide firstly, an obtained dihydroxy compound is selectively protected by an Nap group at position 4 under the action of dibutyltin oxide and bromomethyl naphthalene to obtain a compound 5, hydroxyl of the 3-Nap compound 5 is protected by benzyl to generate a compound 6, and finally an Nap group of the compound 6 is removed by DDQ to obtain a 3-OH compound 7.

Specific Test Operation and Steps:

Compound 5: the ally 2-deoxy-2 azido-L-fucoside 4 (500 mg, 2.2 mmol) is dissolved in anhydrous toluene (22 ml), and then the dibutyltin oxide (814 mg, 3.3 mmol) is added. A reaction liquid is heated to 110° C. and stirred for 1 h, then the reaction liquid is cooled to 40° C., the bromomethyl naphthalene (814 mg, 3.3 mmol) and tetrabutylammonium bromide (1.05 mg, 3.3 mmol) are added, and the reaction is continued for 20 h. After complete reaction, ethyl acetate (30 ml) is added for diluting and washed by saturated salt water. An organic phase is separated and purified by a silicagel column (petroleum ether/ethyl acetate, 5:1) after concentrating to obtain the compound 5 (527 mg, 1.7 mmol, 79%). $[\alpha]_D^{20}$=34.0° (c=1.00, CHCl3); 1H NMR (400 MHz, Chloroform-d) δ 7.85 (dt, J=10.5, 7.7 Hz, 4H, Ar—H), 7.59-7.45 (m, 3H, Ar—H), 5.94 (ddt, J=16.8, 10.9, 5.6 Hz, 1H, Ally-H), 5.33 (dd, J=17.2, 1.7 Hz, 1H, Ally-CH$_{2a}$), 5.21 (dd, J=10.5, 1.5 Hz, 1H, Ally-CH$_{2b}$), 4.88 (s, 2H, 2Nap-H), 4.12 (dd, J=12.9, 6.2 Hz, 1H, Ally-H), 4.23 (d, J=8.1 Hz, 1H, 1-H), 4.12 (dd, J=12.9, 6.2 Hz, 1H, Ally-OCH$_{2b}$), 3.74 (d, J=3.3 Hz, 1H, 4-H), 3.66 (dd, J=10.0, 8.0 Hz, 1H, 2-H), 3.47 (q, J=6.5 Hz, 1H, 5-H), 3.35 (dd, J=10.0, 3.3 Hz, 1H, 3-H), 2.32 (s, 1H, 4-OH), 1.34 (d, J=6.4 Hz, 6-CH$_3$). $^{13}$C NMR (101 MHz, CDCl$_3$) δ 134.65, 133.65, 133.20, 128.55, 127.93, 127.77, 126.98, 126.33, 126.22, 125.75, 117.61, 100.75, 79.41, 77.33, 77.22, 77.01, 76.70, 72.19, 70.19, 69.97, 68.34, 62.57, 16.33. HRMS(ESI) m/z calcd for C$_{20}$H$_{23}$N$_3$O$_4$Na[M+Na]$^+$ 391.1581, found 391.1564.

Compound 6: the compound 5 (527 mg, 1.7 mmol) is dissolved in anhydrous DMF (17 ml) and cooled to 0° C. with ice bath for 30 min. NaH (140 mg, 3.4 mmol) is added into a reaction bottle and continuously stirred at 0° C. for 30 min. and benzyl bromide (0.5 ml, 3.4 mmol) is added. A reaction liquid is recovered to the room temperature and continued to be stirred for 4 h, after reaction raw materials all disappear, DCM (20 ml) is added for diluting, and the reaction is quenched by ice water. Washing is conducted with saturated NaHCO$_3$ three times, and organic phases are combined and purified by the silicagel column (petroleum ether/ethyl acetate, 25:1) after concentrating to obtain the compound 6 (531 mg, 1.2 mmol, 68%). [α]$_D^{20}$=50.3° (c=1.00, CHCl$_3$). $^1$H NMR (400 MHz, Chloroform-d) δ 7.90-7.77 (m, 4H, Ar—H), 7.57-7.45 (m, 3H, Ar—H), 7.38-7.21 (m, 6H, Ar—H), 5.94 (dddd, J=16.9, 10.8, 6.1, 5.0 Hz, 1H, Ally-H), 5.32 (dt, J=17.2, 1.7 Hz, 1H, Ally-H), 5.19 (dq, J=10.5, 1.5 Hz, 1H, Ally-H), 4.97 (d, J=11.7 Hz, 1H, PhCH), 4.87 (s, 2H, 2Nap-H) 4.71 (d, J=11.7 Hz, 1H, PhCH—H), 4.39 (ddt, J=12.9, 5.0, 1.6 Hz, 1H, Ally-H), 4.22 (d, J=8.0 Hz, 1H, 1-H), 4.10 (ddt, J=12.9, 6.1, 1.4 Hz, 1H, Ally-H), 3.87 (dd, J=10.4, 8.0 Hz, 1H, 2-H), 3.55 (d, J=2.8 Hz, 1H, 4-H), 3.42-3.38 (m, 1H, 5-H), 3.36 (dd, J=10.4, 2.8 Hz, 1H, 3-H), 1.20 (d, J=6.4 Hz, 3H, 6-CH$_3$). $^{13}$C NMR (101 MHz, Chloroform-d) δ 138.38, 135.34, 133.93, 133.38, 133.23, 128.55, 128.48, 128.36, 128.07, 127.89, 127.83, 126.79, 126.38, 126.21, 125.90, 117.58, 101.11, 81.07 (C-1), 75.17, 74.85, 72.87, 70.74, 70.07, 63.31, 17.02. HRMS(ESI) m/z calcd for C$_{27}$H$_{29}$N$_3$O$_4$Na[M+Na]$^+$ 482.2050, found 482.2041.

Compound 7: the compound 6 (531 mg, 1.16 mmol) is dissolved in a mixed solvent of dichloromethane (50 ml) and water (5 ml), a reaction liquid is cooled to 0° C., and DDQ (540 mg, 2.32 mmol) is added. The reaction liquid is stirred at the room temperature for 2 h, after complete reaction of all raw materials is monitored by the TLC, the reaction liquid is washed with 10% Na$_2$S$_2$O$_3$, and an organic phase is separated, concentrated after drying with anhydrous sodium sulfate, and purified by the silicagel column (petroleum ether/ethyl acetate, 3:1) to obtain the compound 7 (325 mg, 0.96 mmol, 85%). [α]$_D^{20}$=-3.6° (c=1.00, CHCl$_3$). $^1$H NMR (400 MHz, Chloroform-d) δ 7.42-7.28 (m, 5H, Ar—H), 5.94 (dddd, J=16.7, 10.4, 6.1, 5.1 Hz, 1H, Ally-H), 5.33 (dq, J=17.2, 1.6 Hz, 1H, Ally-H), 5.21 (dq, J=10.5, 1.4 Hz, 1H, Ally-H), 4.81 (d, J=11.6 Hz, 1H, Bn-H), 4.72 (d, J=11.6 Hz, 1H, Bn-H), 4.41 (ddt, J=12.9, 5.1, 1.6 Hz, 1H, Ally-H), 4.26 (d, J=7.7 Hz, 1H, 1-H), 4.11 (ddt, J=12.9, 6.1, 1.4 Hz, 1H, Ally-H), 3.58-3.49 (m, 3H, 2-H, 4-H, 5-H), 3.45 (dd, J=10.4, 3.3 Hz, 1H, 3-H), 2.14 (s, 1H, —OH), 1.31 (d, J=6.5 Hz, 3H, 6-Me). $^{13}$C NMR (101 MHz, Chloroform-d) δ 138.02, 133.75, 128.68, 128.30, 128.18, 117.63, 101.11, 78.60, 76.04, 73.12, 70.95, 70.17, 64.73, 17.01. HRMS(ESI) m/z calcd for C$_6$H$_{21}$N$_3$O$_4$Na[M+Na]$^+$ 342.1424, found 342.1430.

Example 3

Figure 3:
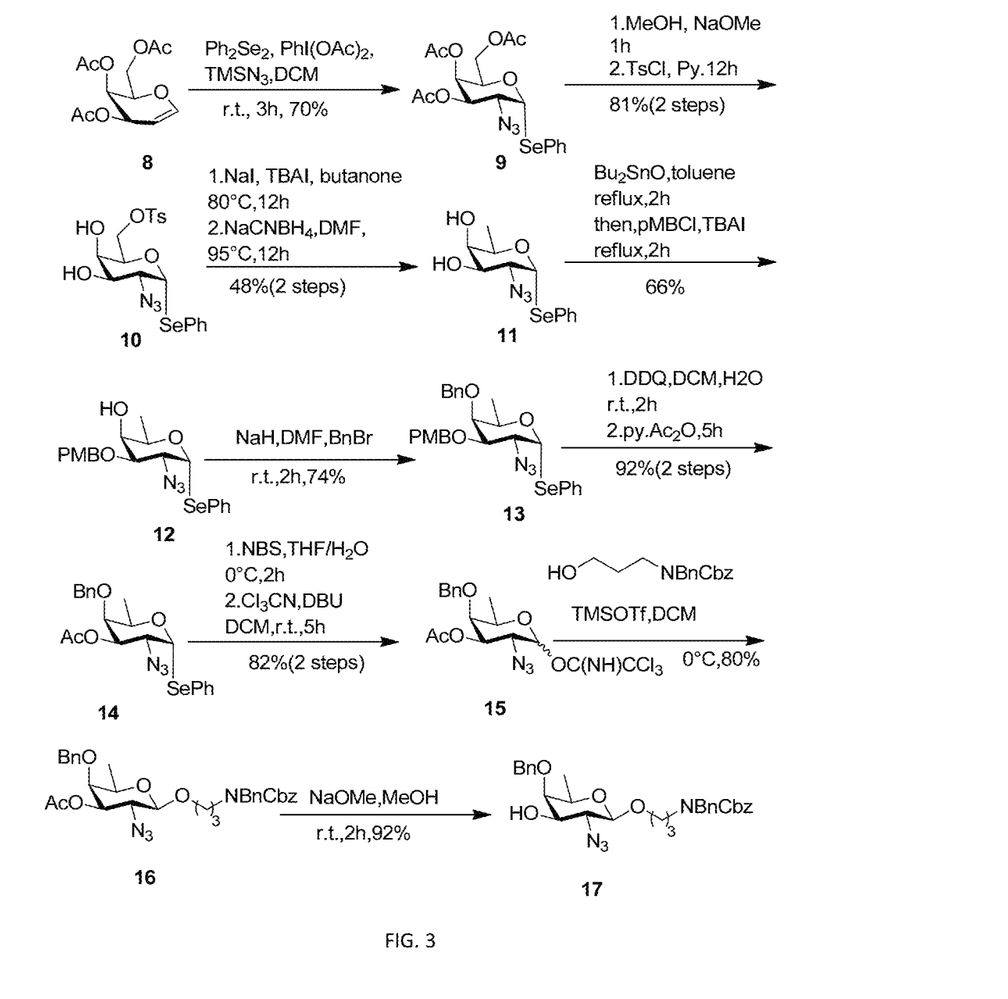
FIG. 3: a synthetic route map of a monosaccharide building block 17 (a D-fucosamine building block)

The synthesis route of a saccharide building block 17 is FIG. 3.

As shown in FIG. 3, 3,4,6-tri-O-acetyl-D-glucal 8 is taken as a starting raw material, and is additively reacted with iodobenzene diacetate (PhI(OAc)$_2$), azido trimethylsilane (TMS-N$_3$) and diphenyl diselenide (Ph$_2$Se$_2$) to obtain a 1-selenophenyl-2-azido compound 9. Three acetyls of the compound 9 are removed with methanol and sodium methoxide, and then hydroxyl at position 6 is selectively protected by 4-toluenesulfonyl chloride (TsCl) to obtain a compound 10. Next, a Ts group of 6-Ts glucose 10 is iodized by sodium iodide, and then the position 6 is reduced to methyl by sodium cyanoborohydride (NaCNBH$_3$) to obtain a D-fucose compound 11. The position 3 of the D-fucose compound is selectively protected by p-methoxybenzyl chloride (PMBCl) and dibutyltin oxide (Bu$_2$SnO) to obtain a compound 12, and then hydroxyl at position 4 is protected by benzyl to obtain a compound 13. Nap at position 4 of the compound 13 is removed by DDQ, and then is protected by acetyl to obtain a compound 14. Selenophenyl at position 1 of the compound 14 is hydrolyzed by tetrabutylammonium bromide (NBS), and then 1-OH fucose is made into a glycosyl trichloroacetimidate donor 15 by Cl$_3$CN and DBU. Then, the compound 15 is reacted with a three-carbon linker arm under the promotion of trimethylsilyl trifluoromethanesulfonate to obtain a fucose compound 16 assembled with the linker arm. Finally, acetyl of the compound 16 is removed in the alkaline environment of methanol and sodium methoxide to obtain the saccharide building block 17.

Specific Test Operation and Steps:

Compound 9: a galactal compound 8 (2.0 g, 7.35 mmol) is dissolved in anhydrous dichloromethane (35 ml), and is then cooled to −30° C. Under the protection of argon, iodobenzene diacetate (2.4 g, 7.35 mmol) and azido trimethylsilane (1.8 ml, 14.7 mmol) are added, continued to be stirred at −30° C. for 0.5 h, then slowly recovered to the room temperature, and the complete reaction of raw materials is monitored by the TLC after continued stirring for 3 h. A reaction liquid is washed with saturated NaHCO$_3$ (20 ml) 3 times, an organic phase is separated, dried by anhydrous sodium sulfate and filtered, and a filtrate is purified by the silicagel column (petroleum ether/ethyl acetate, 6:1) after being spin-dried to obtain the compound 9 (2.4 g, 5.15 mmol, 70%). [α]$_D^{20}$=931.7° (c=1.00, CHCl3). $^1$H NMR (400 MHz, Chloroform-d) δ 7.78-7.11 (m, 5H, Ar—H), 6.01 (d, J=5.4 Hz, 1H, H-1), 5.47 (dd, J=3.4, 1.4 Hz, 1H, 4-H), 5.12 (dd, J=10.9, 3.3 Hz, 1H, 3-H), 4.67 (ddd, J=7.1, 5.8, 1.3 Hz, 1H, 5-H), 4.26 (dd, J=10.9, 5.4 Hz, 1H, 2-H), 4.08 (dd, J=11.5, 5.9 Hz, 1H, 6a-H), 4.02 (dd, J=11.4, 7.1 Hz, 1H, 6b-H), 2.15 (s, 3H, COCH$_3$), 2.07 (s, 3H, COCH$_3$), 1.98 (s, 3H, COCH$_3$). $^{13}$C NMR (101 MHz, Chloroform-d): δ 169.93, 137.08, 135.12, 129.91, 129.19, 128.56, 128.23, 128.04, 127.97, 84.44, 77.22, 75.34, 73.68, 73.44, 70.09, 67.05, 58.99, 21.67, 20.83. HRMS(ESI) m/z calcd for C$_{18}$H$_{21}$N$_3$NaO$_7$Se[M+Na]$^+$ 494.0442.

Compound 10: the compound 9 (0.5 g, 1.1 mmol) is dissolved in methanol (2.2 ml), and sodium methoxide (29 mg, 0.5 mmol) is added. A reaction liquid is stirred at the room temperature for 2 h, and TLC detection shows that raw materials are completely reacted. The reaction liquid is neutralized to about 7 by hydrogen-type Amberlite IR 120 resin. The resin is filtered, and a solvent is spin-dried.

A crude product in the previous step is dissolved in anhydrous pyridine (8 ml), and TsCl (253 mg, 1.3 mmol) is added under the protection of argon. A reaction liquid is stirred at the room temperature for 12 h, and the complete reaction of raw materials is detected by the TLC. The reaction liquid is diluted with DCM, washed with 1 M hydrochloric acid, and then extracted by saturated sodium bicarbonate. Organic phases are combined, dried by anhydrous sodium sulfate, and purified by the silicagel column (dichloromethane/methanol, 200:1) after concentrating to obtain the compound 10 (384 mg, 0.77 mmol, 70%). $[\alpha]_D^{20}$=133.6° (c=1.00, CHCl$_3$). $^1$H NMR (400 MHz, Chloroform-d) δ 7.72 (d, J=8.3 Hz, 2H, Ar—H), 7.58 (dt, J=6.7, 1.6 Hz, 2H, Ar—H), 7.36-7.23 (m, 6H, Ar—H), 5.86 (d, J=5.3 Hz, 1H, H-1), 4.57-4.50 (m, 1H, 5-H), 4.29 (dd, J=10.6, 6.0 Hz, 1H, 6$_a$), 4.10-3.93 (m, 3H, H-2, H-4, 6$_b$-H), 3.78 (ddd, J=9.8, 6.0, 3.3 Hz, 1H, H-3), 2.68 (dd, J=6.5, 4.8 Hz, 2H, 3-OH, 4-OH), 2.44 (s, 3H, PhCH$_3$). $^{13}$C NMR (101 MHz, CDCl$_3$) δ 145.20, 135.04, 132.36, 132.11, 132.01, 129.94, 129.24, 128.78, 128.66, 128.24, 128.00, 127.67, 84.62, 77.34, 77.22, 77.02, 76.70, 70.62, 69.97, 67.87, 67.55, 61.57, 21.68. HRMS(ESI) m/z calcd for C$_{19}$H$_{21}$N$_3$NaO$_5$SSe[M+Na]$^+$ 506.0265.

Compound 11: under the protection of argon, the compound 10 (380 mg, 0.76 mmol) is dissolved in 2-butanone (9.6 ml), and sodium iodide (568 mg, 3.8 mmol) is added. A reaction liquid is stirred at 80° C. for 12 h, and the complete reaction of raw materials is detected by the TLC. The reaction liquid is recovered to the room temperature, ethyl acetate (10 ml) is added for diluting, and the reaction liquid is washed with 10% sodium thiosulfate twice and washed with water twice. Organic phases are combined, dried by anhydrous sodium sulfate, and purified by the silicagel column (petroleum ether/ethyl acetate, 4:1) after concentrating to obtain a new compound (259 mg, 0.57 mmol, 75%). $[\alpha]_D^{20}$=317.6° (c=1.00, CHCl$_3$). $^1$H NMR (400 MHz, Chloroform-d) δ 7.61-7.43 (m, 4H, Ar—H), 7.39-7.12 (m, 6H, Ar—H), 5.96 (d, J=5.3 Hz, 1H, 1-H), 4.44-4.33 (m, 1H, 5-H), 4.22 (d, J=3.7 Hz, 1H, 4-H), 4.09 (dd, J=10.2, 5.3 Hz, 1H, 2-H), 3.79 (ddd, J=9.9, 6.1, 3.3 Hz, 1H, 3-H), 3.17 (dd, J=12.7, 8.2 Hz, 1H, 6-H$_a$), 3.06 (dd, J=12.7, 6.0 Hz, 1H, 6-H$_b$), 2.75 (d, J=6.2 Hz, 1H, 3-OH), 2.45 (d, J=3.9 Hz, 1H, 4-OH). $^{13}$C NMR (101 MHz, CDCl$_3$) δ 134.58, 132.92, 132.87, 132.81, 129.49, 129.32, 129.28, 129.18, 128.19, 127.97, 127.46, 85.04, 84.62, 77.36, 77.25, 77.04, 76.73, 72.32, 71.32, 68.93, 61.71, 26.94. HRMS(ESI) m/z calcd for C$_{12}$H$_{14}$IN$_3$NaO$_3$Se[M+Na]$^+$ 477.9143.

Under the protection of argon, the new compound is dissolved in DMF (2 ml), sodium cyanoborohydride (48 mg, 0.75 mmol) is added. A reaction liquid is stirred at 95° C. for 12 h, and the complete reaction of raw materials is detected by the TLC. The reaction liquid is recovered to the room temperature and washed with water and ethyl acetate. Organic phases are combined, dried with anhydrous sodium sulfate, and purified by the silicagel column (petroleum ether/ethyl acetate, 2:1) after concentrating to obtain the compound 11 (35 mg, 0.1 mmol, 70%). $[\alpha]_D^{20}$=259.4° (c=1.00, CHCl$_3$). $^1$HNMR (400 MHz, Chloroform-d) δ 7.73-7.45 (m, 2H, Ar—H), 7.40-6.93 (m, 3H, Ar—H), 5.92 (d, J=5.3 Hz, 1H, H-1), 4.39 (dt, J=7.4, 6.0 Hz, 1H, 5-H), 4.05 (dd, J=10.0, 5.3 Hz, 1H, 2-H), 3.91-3.74 (m, 2H, H-3. 4-H), 2.60 (d, J=6.3 Hz, 1H, 3-OH), 2.26 (d, J=4.0 Hz, 1H, 4-OH), 1.27 (d, J=6.6 Hz, 3H, 6-CH$_3$). $^{13}$C NMR (101 MHz, Chloroform-d) δ 134.48, 129.15, 127.90, 85.00, 77.22, 71.46, 71.29, 68.69, 61.88, 15.98. HRMS(ESI) m/z calcd for C$_{12}$H$_{15}$N$_3$NaO$_3$Se[M+Na]$^+$ 346.0230, found 346.0226.

Compound 12: the compound 11 (3.0 g, 9.1 mmol) is dissolved in anhydrous toluene (54 ml), and Bu$_2$SnO (3.5 g, 13.7 mmol) is added under the protection of argon. A reaction liquid is heated to 118° C. and stirred for 1.5 h for reflux. The reaction liquid is then cooled to 60° C., PMBCl (1.9 ml, 13.7 mmol) and TBAI (5.1 g, 13.7 mmol) are added, the reaction liquid is continued to be stirred for 2 h. The reaction liquid is cooled to the room temperature, ethyl acetate (80 ml) is added for diluting, the reaction liquid is washed with water (100 ml) 2 times, an organic phase is separated and dried by anhydrous sodium sulfate, a filtrate is purified by the silicagel column (petroleum ether/ethyl acetate, 6:1) after concentrating to obtain the compound 12 (2.7 g, 6 mmol, 66%). $[\alpha]_D^{20}$=137.9° (c=1.00, CHCl3). 1H NMR (400 MHz, Chloroform-d) δ 7.26 (s, 11H, Ar—H), 5.88 (d, J=5.4 Hz, 1H, H-1), 4.70 (d, J=11.0 Hz, 1H, Bn-H), 4.63 (d, J=11.0 Hz, 1H, Bn-H), 4.36-4.24 (m, 1H, 5-H), 4.15 (dd, J=10.2, 5.3 Hz, 1H, 2-H), 3.86 (dt, J=3.2, 1.5 Hz, 1H, 4-H), 3.82 (s, 3H, Me-H), 3.69 (dd, J=10.2, 3.2 Hz, 1H, 3-H), 2.35 (t, J=1.6 Hz, 1H, 4-OH), 1.26 (d, J=6.6 Hz, 3H, 6-Me). $^{13}$C NMR (101 MHz, Chloroform-d) δ 159.74, 134.40, 129.75, 129.10, 129.08, 127.75, 114.14, 85.28, 78.85, 71.84, 68.61, 68.55, 60.18, 55.31, 16.05. HRMS(ESI) m/z calcd for C$_{20}$H$_{23}$N$_3$O$_4$SeNa [M+Na]$^+$ 472.0751, found 472.0725.

Compound 13: the compound 12 (2.2 g, 4.9 mmol) is dissolved in DMF (30 ml) and stirred at 0° C. for 30 min, and sodium hydride (396 mg, 9.8 mmol) is slowly transferred under the protection of argon. Stirring is continued in ice bath for 30 min, benzyl bromide (1.2 ml, 9.8 mmol) is dropwise added into the reaction liquid. Stirring is continued for 2 h for reaction, the complete reaction of all raw materials is detected by the TLC, the reaction is quenched by adding ice water, the reaction liquid is diluted with DCM and dried with the anhydrous sodium sulfate after extraction, and a concentrated liquid is purified by the silicagel column (petroleum ether/ethyl acetate, 30:1) to obtain the compound 13 (1.9 g, 3.6 mmol, 74%). $[\alpha]_D^{20}$=71.5° (c=1.00, CHCl$_3$). $^1$HNMR (400 MHz, Chloroform-d) δ 7.57-7.55 (m, 2H, Ar—H), 7.36-7.25 (m, 10H, Ar—H), 6.94-6.91 (m, 2H, Ar—H), 5.92 (d, J=5.3 Hz, 1H, H-1), 4.94 (d, J=11.4 Hz, 1H, PhCH), 4.77-4.66 (m, 2H, PhCH2), 4.60 (d, J=11.5 Hz, 1H, PhCH), 4.33 (dd, J=10.2, 5.3 Hz, 1H, H-2), 4.21 (q, J=6.5 Hz, 1H, H-5), 3.83 (s, 3H, OCH$_3$), 3.71 (dd, J=10.3, 2.7 Hz, 1H, H-3), 3.68 (dd, J=2.8, 1.1 Hz, 1H, H-4), 1.12 (d, J=6.4 Hz, 3H, 6-CH3). $^{13}$C NMR (101 MHz, CDCl3) δ 159.63, 138.33, 134.48, 129.72, 129.16, 128.90, 128.44, 128.32, 127.90, 127.77, 114.14, 85.79, 80.47, 77.16, 76.01, 75.13, 72.40, 69.56, 61.03, 55.46, 16.69. HRMS(ESI) m/z calcd for C$_{27}$H$_{29}$N$_3$NaO$_4$Se [M+Na]$^+$ 562.1221, found 562.1209.

Compound 14: the compound 13 (900 mg, 1.67 mmol) is dissolved in DCM (84 ml), and 2,3-dichloro-5,6-dicyano-1,4-benzoquinone (564 mg, 2.5 mmol) and water (4.2 ml) are added under the protection of argon. The reaction is stirred at the room temperature for 7 h, and complete reaction is detected by the TLC. DCM (50 ml) is added for diluting, and a reaction liquid is washed with 10% sodium thiosulfate (100 ml) twice. An organic phase is separated, dried with anhydrous sodium sulfate, and purified by the silicagel column (petroleum ether/ethyl acetate, 10:1) after concentrating to obtain a new product (573 mg, 1.4 mmol, 82%). The new product is dissolved in dried pyridine (3.2 ml) and cooled to 0° C., acetic anhydride (0.5 ml, 5.12 mmol) is slowly added after 30 min, a reaction liquid is recovered to the room temperature and continued to be stirred for 5 h, and the complete reaction of raw materials is detected by the TLC. The reaction liquid is washed with 1 M hydrochloric acid, and is then extracted by saturated sodium bicarbonate and salt water. An organic phase is separated and purified by the silicagel column (petroleum ether/ethyl acetate=20:1)

after concentrating to obtain the compound 14 (598 mg, 1.3 mmol, quant). $^1$H NMR (400 MHz, Chloroform-d) δ 7.68-7.21 (m, 9H, Ar—H), 5.91 (d, J=5.3 Hz, 1H, H-1), 5.46 (dd, J=3.3, 1.2 Hz, 1H, H-4), 4.75 (d, J=10.7 Hz, 1H, PhCH$_2$), 4.53 (d, J=10.7 Hz, 1H, PhCH), 4.48-4.37 (m, 1H, H-5), 4.12 (dd, J=10.3, 5.4 Hz, 1H, H-2), 3.78 (dd, J=10.4, 3.3 Hz, 1H, H-3), 2.15 (s, 3H, COCH$_3$), 1.12 (d, J=6.5 Hz, 3H, 6-CH$_3$). $^{13}$C NMR (101 MHz, Chloroform-d) δ 170.52, 136.90, 134.53, 129.12, 128.50, 128.34, 128.07, 127.88, 85.08, 71.68, 68.89, 67.77, 60.36, 20.76, 16.07. HRMS(ESI) m/z calcd for C$_{21}$H$_{23}$N$_3$NaO$_4$Se [M+Na]$^+$ 484.0751, found 484.0749.

Compound 15: the compound 14 (580 mg/1.3 mmol) is dissolved in a mixed solution of tetrahydrofuran (6 ml) and water (6 ml), and cooled to 0° C. Tetrabutylammonium bromide (3 mmol) is added, a reaction liquid is recovered to the room temperature and continued to be stirred for 5 h, and TLC detection shows that raw materials are completely reacted. The reaction liquid is washed with 10% sodium thiosulfate and extracted by DCM and water, an organic phase is separated, dried with anhydrous sodium sulfate, and purified by the silicagel column (petroleum ether/ethyl acetate, 4:1) after concentrating to obtain a new compound (417 mg, 1.3 mmol, quant). [α]$_D^{20}$=54.9° (c=1.00, CHCl$_3$). $^1$H NMR (400 MHz, Chloroform-d) δ 7.43-7.30 (m, 8H, Ar—H), 5.47 (dd, J=3.3, 1.3 Hz, 1H, 1a-H), 5.34 (dd, J=3.4, 1.1 Hz, 1H, 4b-H), 5.32 (d, J=3.6 Hz, 1H, 4a-H), 4.77 (d, J=10.8 Hz, 1H, PhCH), 4.75 (d, J=11.1 Hz, 0.8H, PhCH), 4.54 (d, J=7.9 Hz, 1H, 1b-H), 4.53 (d, J=10.8 Hz, 1H, PhCH), 4.53 (d, J=11.1 Hz, 0.8H, PhCH), 4.32 (qd, J=6.6, 1.3 Hz, 1H, 5-H), 4.03 (dd, J=10.5, 3.2 Hz, 1H, 2a-H), 3.74 (dd, J=10.5, 3.5 Hz, 1H, 3a-H), 3.69 (td, J=6.4, 1.1 Hz, 0.8H, 5b-H), 3.58 (dd, J=10.2, 7.9 Hz, 0.8H, 2b-H), 3.45 (dd, J=10.3, 3.4 Hz, 0.8H, 3b-H), 2.19 (s, 2.4H, COCH$_3$), 2.18 (s, 3H, COCH$_3$), 1.25 (d, J=6.5 Hz, 2.4H, 6b-CH$_3$), 1.19 (d, J=6.5 Hz, 3H, 6a-CH$_3$). $^{13}$C NMR (101 MHz, CDCl3) δ 170.90, 170.88, 137.15, 137.04, 128.63, 128.52, 128.40, 128.22, 128.17, 96.20, 92.46, 77.91, 77.48, 77.36, 77.16, 77.16, 76.84, 74.36, 71.91, 71.67, 69.69, 69.46, 68.39, 65.21, 64.03, 59.82, 20.95, 20.93, 16.55, 16.42. HRMS(ESI) m/z calcd for C$_{15}$H$_{19}$N$_3$O$_5$Na [M+Na]$^+$ 344.1217, found 344.1208.

The new compound (417 mmol, 1.3 mmol) is dissolved in anhydrous dichloromethane (14 ml) and cooled to 0° C. Trichloroacetonitrile (0.4 ml, 3.78 mmol) and DBU (23 μL, 0.13 mmol) are sequentially added, a reaction liquid is continued to be stirred for 5 h, and the complete reaction of raw materials is detected by the TLC. The reaction liquid is directly concentrated at the room temperature, and purified by the silicagel column (petroleum ether/ethyl acetate, 10:1) to obtain the compound 15 (518 mg, 1.1 mmol, 88%).

Compound 16: glycosyl trichloroacetimidate 15 (518 mg, 1.1 mmol) and n-benzyl-n-benzyl formate-propanol (500 mg, 1.7 mmol) are dissolved in anhydrous DCM, 4 Å molecular sieves are added and stirred at the room temperature for half an hour. Then a reaction liquid is cooled to −40° C., and TMSOTf (0.3 ml, 1.3 mmol) is slowly added under argon. The reaction liquid is continued to be stirred at −40° C. for 4 h, the complete reaction of raw materials is monitored by the TLC, and the reaction is quenched by triethylamine (1 ml). The reaction liquid is extracted by saturated NaHCO$_3$, an organic phase is separated, dried with anhydrous Na$_2$SO$_4$, and purified by the silicagel column to obtain the compound 16 (396 mg, 0.44 mmol, 60%). [α]$_D^{20}$=−10.8° (c=1.00, CHCl$_3$). $^1$H NMR (400 MHz, Chloroform-d) δ 7.45-7.16 (m, 15H, Ar—H), 5.23-5.12 (m, 2H, PhCH), 4.74-4.59 (m, 3H, 3-H, 2PhCH), 4.61-4.38 (m, 2H, 2NPhCH), 4.21 (dd, J=33.3, 8.0 Hz, 1H, 1-H), 4.02-3.87 (m, 1H, linker-OCH), 3.79 (t, J=9.5 Hz, 1H 2-H), 3.67 (d, J=3.0 Hz, 1H, 4-H), 3.63-3.27 (m, 4H, 5-H linker-OCH, linker-NCH$_2$), 2.07 (s, 3H, COCH$_3$), 2.01-1.76 (m, 2H, linker-CH$_2$), 1.24 (d, J=6.4 Hz, 3H, 6-CH3). $^{13}$C NMR (101 MHz, CDCl$_3$) δ 170.38, 137.95, 137.70, 128.52, 128.46, 128.40, 128.32, 127.97, 127.92, 127.87, 127.27, 101.99, 77.37, 77.25, 77.05, 76.74, 76.19, 75.59, 74.23, 70.48, 67.40, 67.19, 61.11, 50.90, 44.67, 43.62, 28.48, 28.03, 20.89, 16.57. HRMS(ESI) m/z calcd for C$_{33}$H$_{38}$N$_4$O$_7$Na[M+Na]$^+$ 625.2633, found 625.2650.

Compound 17: the compound 16 (262 mg, 0.42 mmol) is dissolved in methanol (4 ml), and sodium methoxide (40 mg) is added. A reaction liquid is stirred at the room temperature for 2 h, after raw materials are all completely reacted, the reaction liquid is diluted with methanol, and the reaction liquid is neutralized to pH about 7 by hydrogen-type Amberlite IR 120 resin. The resin is filtered, and a filtrate is purified by the silicagel column (petroleum ether/ethyl acetate, 3:1) after concentrating to obtain the compound 17 (244 mg, 0.42 mmol, quant). [α]$_D^{20}$=−24.1° (c=1.00, CHCl$_3$). $^1$H NMR (400 MHz, Chloroform-d) δ 7.76-6.87 (m, 15H, Ar—H), 5.22 (d, J=9.4 Hz, 2H, PhCH), 4.83 (d, J=11.6 Hz, 1H, PhCH), 4.78 (d, J=11.6 Hz, 1H, PhCH), 4.58 (d, J=14.0 Hz, 2H, PhCH), 4.25-4.08 (m, 1H, 1-H), 4.05-3.86 (m, 1H, linker-OCH), 3.62-3.34 (m, 7H, 2-H, 3-H, 4-H, 5-H, linker-OCH, linker-NCH2), 2.46 (s, 1H, —OH), 2.02-1.80 (m, 2H, linker-CH$_2$), 1.31 (d, J=6.4 Hz, 3H, 6-CH$_3$). $^{13}$C NMR (101 MHz, Chloroform-d) δ 138.00, 128.58, 128.56, 128.50, 128.26, 128.08, 127.95, 127.89, 102.12 (1-C), 78.48, 77.36, 75.94, 72.96, 70.84, 67.24, 64.70, 50.94, 43.74, 28.58, 16.91. HRMS(ESI) m/z calcd for C$_{31}$H$_{36}$N$_4$NaO$_6$ [M+Na]$^+$ 583.2527, found 583.2531.

Example 4: Study on Synthesis Method of D-Fucose Building Block

Figure 4:
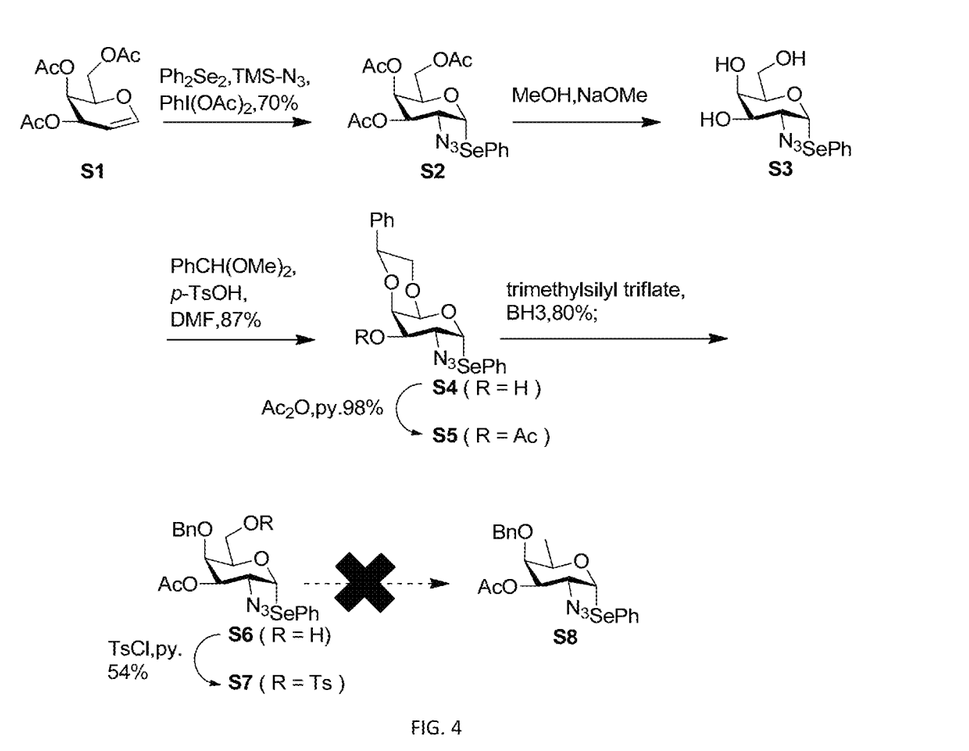
FIG. 4: a synthetic route map of a first construction method of the monosaccharide building block 17.

Method I:

According to synthesis methods of similar compounds reported in literature, the method 1 for synthesizing the D-fucose building block is summarized, as shown in FIG. 4. Galactal S1 is used as a starting raw material, under the joint action of diphenyl diselenide, trimethylsilyl azide and diacetyl iodobenzene, selenophenyl and azide are introduced into positions 1 and 2 respectively, an important intermediate S2 is obtained, under the action of methanol sodium methoxide, acetyls at positions 3, 4 and 6 are removed to obtain a compound S3, then benzylidene groups are introduced into positions 4 and 6 to obtain a compound S4, then position 3 is protected by acetyl temporarily to obtain a compound S5, under the joint action of trimethylsilyl trifluoromethane sulfonic acid and borane, the benzylidene groups are selectively opened, benzyl is introduced to position 4 to obtain a compound S6, p-toluenesulfonyl is introduced into the exposed position 6 under the action of p-toluenesulfonyl chloride and pyridine to obtain a compound S7, however, when the p-toluenesulfonyl at position 6 is replaced by an iodine atom, the reaction cannot proceed smoothly.

An inventor tries different conditions, including: acetonitrile and TBAI reacted at 100° C. and 80° C. respectively, and butanone and sodium iodide reacted at 80° C., but they fail to introduce iodine into position 6 to obtain a corresponding product S8, and thus the target D-fucose building block cannot be synthesized along the route.

Figure 5:
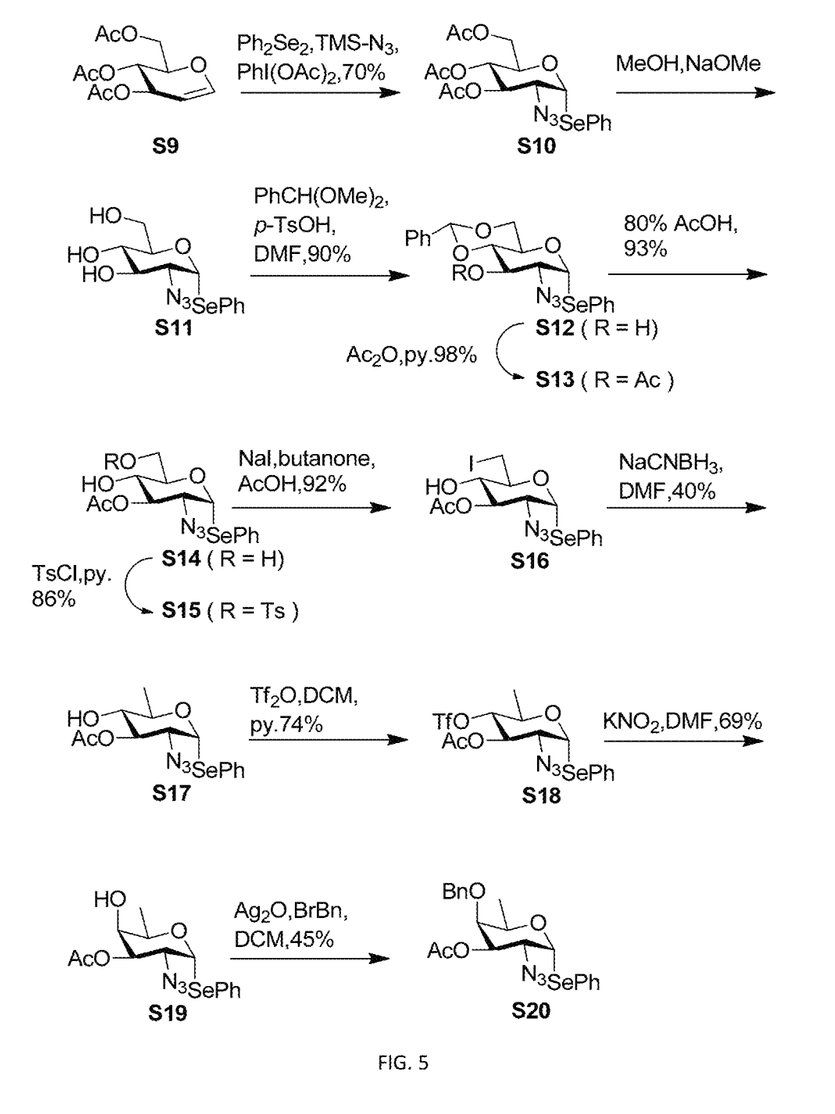
FIG. 5: a synthetic route map of a second construction method of the monosaccharide building block 17.

Method II:

The method I is improved, and the improved synthesis route is as shown in FIG. 5. Peracetyl-D-glucal S9 is taken as a starting raw material, a free radical addition reaction is used, selenophenyl and azido are introduced into positions 1 and 2 respectively to obtain a compound S10, then a compound S11 is obtained after deacetylating, positions 4 and 6 are simultaneously protected to obtain a compound S12, position 3 is protected temporarily by the acetyl to obtain a compound S13, and then the benzylidene groups are opened in a 80% acetic acid solution to obtain a compound S14, p-toluenesulfonyl is introduced into position 6 under the conditions of p-toluenesulfonic acid and pyridine to obtain a compound S15, then in a reflux solution of 2-butanone, it reacts with sodium iodide, and iodine is introduced into position 6 to obtain a compound S16. Hydroxyl at position 6 of the compound S16 is reduced to methyl by a reduction method of sodium cyanoborohydride to obtain a compound S17, then trifluoromethylsulfonyl is introduced into position 4 firstly to obtain a compound S18, and then reduction is conducted by potassium nitrite to obtain a compound S19 with vertical hydroxyl at position 4, that is, the horizontal hydroxyl at position 4 is successfully transformed into the hydroxyl with a vertical bond, thus is transformed into a D-fucose configuration, then under the neutral condition of silver oxide, and benzyl is introduced into hydroxyl at position 4 to obtain a compound S20.

Although this method can obtain the required compound S20, the practicability is not high, which is mainly reflected in the long route steps, a total of 11 reaction modules, especially in the 4-OH transposition and the last step using an OBn group on $Ag_2O$, the reaction yield of the two steps both are less than 50%, so that the total yield of this route is less than 2%.

Example 5

Figure 6:
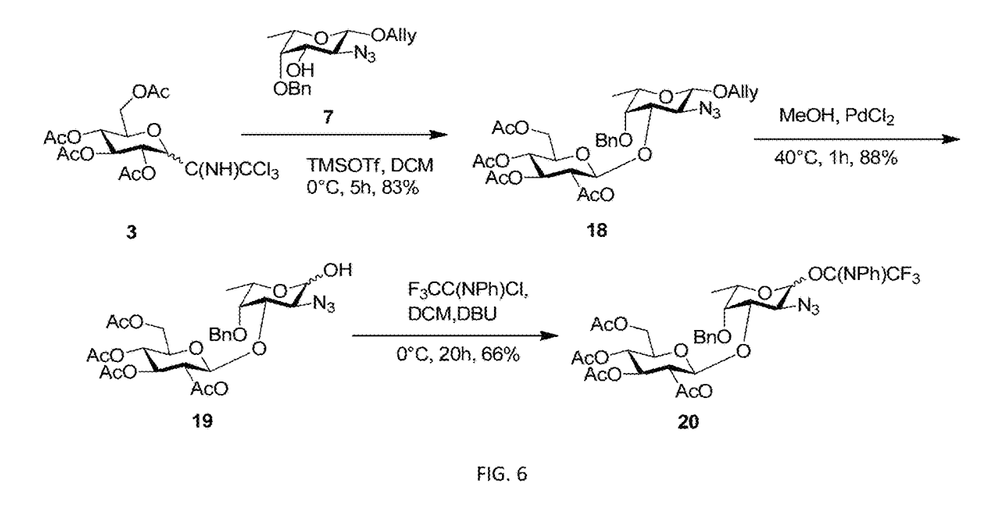
FIG. 6: a synthetic route map of a disaccharide 20.

A synthesis route of a disaccharide 20 is FIG. 6.

As shown in FIG. 6, the synthesis of a disaccharide 18 relies on the glucose compound 3 previously synthesized by the route of FIG. 1 and the L-fucose compound 7 synthesized by the route of FIG. 2 under the catalysis of Lewis acid TMSOTf. Then, allyl at the reducing end of the disaccharide 18 is hydrolyzed by palladium chloride in a methanol solution to obtain a 1-OH disaccharide compound 19. Finally, the compound 19 is made into a disaccharide donor 20 containing N-phenyl-trifluoroacetimidate by 2,2,2-trifluoro-N-phenylacetimidoyl chloride.

Specific Test Operation and Steps:

Compound 18: a monosaccharide donor 3 (500 mg, 1.0 mmol) and a glycosyl receptor 7 (165 mg, 0.52 mmol) are dissolved in anhydrous DCM (10 ml) under the protection of nitrogen, and 4 Å molecular sieves are added. A reaction liquid is stirred at the room temperature for 30 min, and then cooled to 0° C., and TMSOTf (36 μL, 0.2 mmol) is added. The reaction liquid is slowly recovered to the room temperature and continued to be stirred for 5 h, and TLC detection shows that raw materials are completely reacted. The reaction liquid is quenched by triethylamine and extracted by a saturated sodium bicarbonate solution, and a filtrate is purified by a silicagel column (petroleum ether/ethyl acetate, 2:1) to obtain the compound 18 (300 mg, 0.46 mmol, 88%). $[\alpha]_D^{20}$=2.3° (c=1.00, $CHCl_3$). $^1$H NMR (400 MHz, Chloroform-d) δ 7.52-6.73 (m, 6H, Ar—H), 5.84 (ddt, J=16.4, 10.8, 5.6 Hz, 1H, Ally-H), 5.23 (d, J=17.3 Hz, 1H, Ally-H), 5.17-5.05 (m, 3H, Ally-H, 3'-H, 4'-H), 5.03 (t, J=8.2 Hz, 1H, 2'-H), 4.80 (d, J=11.3 Hz, 1H, Bn-H), 4.77 (d, J=7.7 Hz, 1H, 1'-H), 4.46 (d, J=11.4 Hz, 1H, Bn-H), 4.29 (dd, J=13.0, 5.0 Hz, 1H, Ally-H), 4.20 (dd, J=12.3, 4.4 Hz, 1H, 6'-Ha), 4.17-4.08 (m, 2H, 6'-Hb, 1-H), 4.00 (dd, J=13.0, 6.2 Hz, 1H, Ally-H), 3.66 (qd, J=10.3, 4.9 Hz, 3H, 5'-H, 2-H, 3-H), 3.43 (d, J=2.5 Hz, 1H, 4-H), 3.35 (d, J=6.4 Hz, 1H, 5-H), 1.99 (s, 3H, $CH_3CO$), 1.95 (s, 3H, $CH_3CO$), 1.92 (s, 3H, CH3CO), 1.79 (s, 3H, $CH_3CO$), 1.10 (d, J=6.3 Hz, 3H, 6-$CH_3$). $^{13}$C NMR (101 MHz, Chloroform-d) δ 170.38, 170.08, 169.04, 168.88, 137.76, 133.47, 128.04, 127.91, 127.52, 117.24, 100.54, 98.46, 79.37, 77.03, 75.44, 74.68, 72.99, 71.87, 71.34, 70.06, 69.76, 68.00, 61.87, 61.62, 20.46, 20.32, 16.50. HRMS(ESI) m/z calcd for $C_{30}H_{39}N_3O_{13}$ [M+Na]$^+$ 672.2375, found 672.2377.

Compound 19: the compound 18 (300 mg, 0.46 mmol) is dissolved in anhydrous methanol (23 ml), and then a reaction liquid is heated to 40° C. Palladium chloride (16 mg) is added, stirring is continued for 1 h, and the complete reaction of raw materials is detected by the TLC. The reaction liquid is diluted with DCM and extracted by the saturated sodium bicarbonate, an organic phase is separated and purified by the silicagel column (petroleum ether/ethyl acetate, 1:1) after concentrating to obtain the compound 19 (256 mg, 0.40 mmol, 88%). $[\alpha]_D^{20}$=−7.1° (c=1.00, $CHCl_3$). $^1$H NMR (400 MHz, Chloroform-d). -anomer δ 7.35-7.22 (m, 5H, Ar—H), 5.23 (d, J=3.5 Hz, 1H, 1-H), 5.22-5.00 (m, 3H, 2'-H, 3'-H, 4'-H), 4.86-4.72 (m, 2H, 1'-H, Bn-H), 4.43 (d, J=11.0 Hz, 1H, Bn-H), 4.38 (d, J=7.8 Hz, 1H, 1'-H), 4.28 (dd, J=10.6, 2.7 Hz, 1H, 3-H), 4.25-4.11 (m, 2H, 6'-Hab), 4.11-4.02 (m, 1H, 5-H), 3.75-3.65 (m, 2H, 2-H, 5'-H), 3.61 (d, J=2.8 Hz, 1H, 4-H), 2.01 (s, 3H, OAc-Me), 1.97 (s, 3H, OAc-Me), 1.93 (s, 3H, OAc-Me), 1.72 (s, 3H, OAc-Me), 1.10 (d, J=6.4 Hz, 3H, 6-Me). -anomer δ 7.35-7.22 (m, 5H, Ar—H), 5.22-5.00 (m, 3H, 2'-H, 3'-H, 4'-H), 4.80 (d, J=11.5 Hz, 1H, Bn-H), 4.47 (d, J=11.3 Hz, 1H, Bn-H), 4.38 (d, J=7.8 Hz, 1H, 1'-H), 4.22-4.03 (m, 4H, 6ab-H, 1'-H, 3-H), 3.74-3.58 (m, 3H, 2-H, 4-H, 5'-H), 3.51-3.41 (m, 1H, 5-H), 2.01 (s, 3H, OAc-Me), 1.97 (s, 3H, OAc-Me), 1.94 (s, 3H, OAc-Me), 1.72 (s, 3H, OAc-Me), 1.10 (d, J=6.4 Hz, 3H, 6-Me). $^{13}$C NMR (101 MHz, $CDCl_3$) δ 170.79, 170.69, 170.43, 170.38, 169.33, 169.29, 169.15, 169.05, 137.87, 128.44, 128.39, 128.36, 128.32, 128.24, 128.14, 128.12, 128.00, 127.93, 102.18, 101.52, 98.74, 98.67, 98.65, 96.22, 92.72, 79.54, 79.42, 79.37, 77.37, 77.25, 77.14, 77.05, 76.87, 76.73, 76.48, 75.73, 75.52, 75.17, 75.03, 75.00, 74.96, 74.06, 73.33, 73.23, 73.20, 72.13, 72.10, 71.97, 71.82, 71.56, 70.69, 70.62, 70.40, 68.25, 68.20, 66.62, 63.71, 63.53, 62.05, 61.99, 61.78, 58.93, 43.75, 29.68, 20.71, 20.69, 20.66, 20.58, 20.56, 20.54, 16.78, 16.67, 16.61, 16.57. HRMS(ESI) m/z calcd for $C_{27}H_{35}N_3NaO_{13}$ [M+Na]$^+$ 632.2062, found 632.2039.

Compound 20: the compound 19 (86 mg, 0.14 mmol) is dissolved in anhydrous DCM and cooled to 0° C. 2,2,2-trifluoro-N-phenylacetimidoyl chloride (0.1 ml) and DBU (30 μL) are added under the protection of argon. A reaction liquid is recovered to the room temperature, continued to be stirred for 20 h, and purified by the silicagel column (petroleum ether/ethyl acetate, 2.5:1) after concentrating at the room temperature to obtain the compound 20 (67 mg).

Example 6

Figure 7:
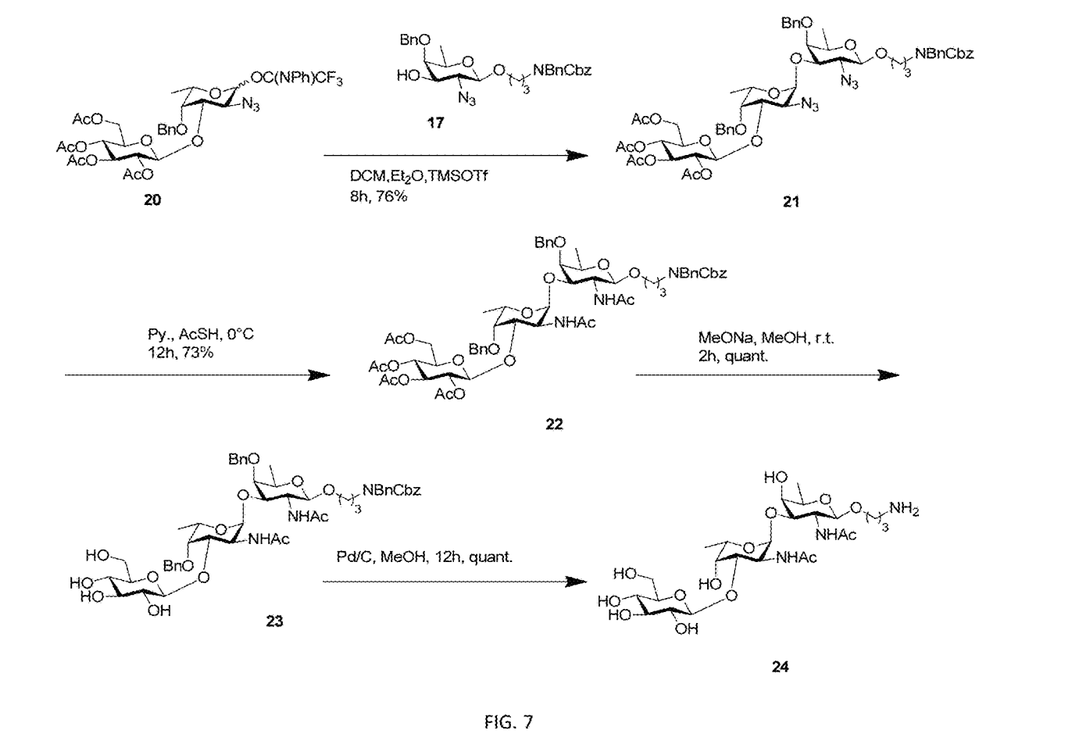
FIG. 7: a synthetic route map of a trisaccharide 24.

A synthesis route of a trisaccharide 24 is FIG. 7.

As shown in FIG. 7, a disaccharide donor 20 and a monosaccharide receptor 17 are catalyzed by Lewis acid TMSOTf to obtain a 1,2-cis linked trisaccharide 21 under the joint action of solvents such as dichloromethane, ether and thiophene. Azido of the trisaccharide 21 is reduced to an acetamido compound 22 at zero degree by thioacetic acid and pyridine. 4 acetyls on a glucose group of the compound 22 are removed under the alkaline condition to obtain a compound 23. Finally, all aromatic groups are removed by palladium carbon and hydrogen to obtain an O-antigen trisaccharide of Pseudomonas aeruginosa serotype O11 assembled with an aminolink.

Specific Test Operation and Steps:

Compound 21: the disaccharide donor 20 (35 mg) and the monosaccharide receptor 17 (45 mg) are dissolved in a mixed solvent of anhydrous DCM (0.9 ml), ether (0.9 ml) and thiophene (0.9 ml) under the protection of argon, 4 Å molecular sieves are added, a reaction liquid is stirred at the room temperature for 30 min, and then cooled to 0° C. TMSOTf is added, stirring is continued for 8 h, and TLC detection shows that the glycosyl donor is completely reacted. The reaction is quenched by triethylamine and extracted by saturated sodium bicarbonate, and an organic phase is purified by a silicagel column (petroleum ether/ethyl acetate, 3:1) and a Sephadex LH-20 gel column (DCM/MeOH, 1:1) after concentrating to obtain the compound 21 (37 mg). $[\alpha]_D^{20}$=−44.5° (c=1.00, CHCl$_3$). $^1$H NMR (400 MHz, Chloroform-d) δ 7.41-7.19 (m, 20H, Ar—H), 5.30-5.04 (m, 6H, 2PhCH, 1'-H, 2"-H, 3"-H, 4"-H), 4.83 (d, J=11.1 Hz, 1H, PhCH), 4.77-4.75 (m, 3H, 2PhCH, 1"-H), 4.55-4.50 (m, 2H, NPhCH), 4.42 (d, J=11.0 Hz, 1H, PhCH), 4.33-4.21 (m, 1H, 6"-H), 4.18 (d, J=7.0 Hz, 1H, 1-H), 4.07 (m, 2H, 3'-H, 6"-H), 4.00-3.88 (m, 1H, linker-OCH), 3.81 (t, J=9.0 Hz, 1H, 2-H), 3.79-3.67 (m, 2H, 5'-H, 5"-H), 3.62 (dd, J=10.7, 3.7 Hz, 1H, 2'-H), 3.53-3.26 (m, 6H, linker-OCH, linker-NCH$_2$, 3-H, 4H, 4'-H), 2.04 (s, 1H, COCH$_3$), 2.00 (s, 1H, COCH$_3$), 1.96-1.81 (m, 2H, linker-CH$_2$), 1.80 (s, 1H, COCH$_3$), 1.30 (d, J=6.7, 3H, 6-CH$_3$), 1.10 (d, J=6.4 Hz, 3H, 6'-CH$_3$). $^{13}$C NMR (101 MHz, CDCl$_3$) δ 170.70, 170.41, 169.22, 168.95, 138.47, 137.94, 137.78, 128.50, 128.44, 128.38, 127.99, 127.96, 127.89, 127.86, 127.77, 127.62, 127.25, 102.44, 100.52, 99.60, 79.20, 79.11, 77.34, 77.22, 77.02, 76.70, 75.31, 75.26, 73.29, 72.29, 71.96, 70.71, 68.03, 67.50, 67.18, 63.61, 61.76, 58.26, 50.90, 49.78, 44.76, 43.68, 29.69, 28.52, 28.09, 23.42, 20.66, 20.59, 16.95, 16.54. HRMS(ESI) m/z calcd for C$_{58}$H$_{69}$N$_7$NaO$_{18}$[M+Na]$^+$ 1174.4591, found 1174.4626.

Compound 22: the compound 21 (30 mg) is dissolved in dry pyridine (0.5 ml) and thioacetic acid (0.5 ml). A reaction liquid is stirred at 0° C. for 12 h, the complete reaction of raw materials is detected by the TLC, the reaction liquid is subjected to azeotropy with toluene three times, and is then purified by the silicagel column (dichloromethane methanol, 50:1) to obtain the compound 21 (30 mg). $[\alpha]_D^{20}$=49.5° (c=1.00, CHCl$_3$). $^1$H NMR (400 MHz, Chloroform-d) δ 7.80-6.90 (m, 20H, Ar—H), 6.83 (d, J=8.1 Hz, 1H, NHAc—H), 6.18 (d, J=9.2 Hz, 1H, NHAc—H), 5.27-5.13 (m, 3H, 3"-H, 2Cbz-H), 5.10-4.99 (m, 2H, 1'-H, 4"-H), 4.96 (t, J=8.7 Hz, 1H, 2"-H), 4.88 (d, J=11.1 Hz, 1H, Bn-H), 4.84-4.79 (m, 1H, Bn-H), 4.74 (d, J=15.5 Hz, 2H, Bn-H), 4.63 (d, J=8.0 Hz, 3H, 1"-H, 3-H, 2'-H), 4.41 (d, J=10.9 Hz, 1H, Bn-H), 4.34-4.25 (m, 2H, 6"-H, 1-H), 4.25-4.13 (m, 1H, 2-H), 4.09 (t, J=9.0 Hz, 1H, 6"-H), 3.86 (dtt, J=34.7, 10.8, 6.0 Hz, 3H, 5'-H, 4-H, 3'-H), 3.66 (dd, J=9.7, 6.0 Hz, 1H, 5"-H), 3.60-3.52 (m, 1H, 3-H), 3.44 (d, J=7.3 Hz, 2H, 5-H, 4'-H), 3.34-3.08 (m, 1H, linker-OCH$_2$—H), 2.87 (dt, J=14.3, 5.0 Hz, 1H, linker-NH$_2$—H), 2.14 (s, 3H, OAc-Me), 2.09 (s, 3H, NHAc-Me), 2.06 (s, 3H, OAc-Me), 2.00 (s, 3H, OAc-Me), 1.89 (s, 3H, NHAc-Me), 1.80 (s, 3H, OAc-Me), 1.68 (d, J=9.6 Hz, 1H), 1.32 (d, J=6.3 Hz, 3H, 6'-Me), 1.17 (d, J=6.5 Hz, 3H, 6-Me). $^{13}$C NMR (101 MHz, Chloroform-d) δ 171.62, 171.05, 170.77, 170.42, 169.28, 168.83, 156.56, 138.81, 138.17, 137.98, 137.35, 136.86, 128.66, 128.55, 128.51, 128.47, 128.36, 128.17, 128.09, 127.96, 127.91, 127.80, 127.76, 127.71, 127.65, 127.50, 127.28, 127.19, 126.35, 101.24, 100.77, 99.67, 80.00, 79.66, 78.94, 77.83, 77.23, 75.05 (d, J=13.2 Hz), 73.18, 72.20, 72.07, 70.73, 68.21, 67.52, 67.33, 65.76, 61.95, 52.22, 49.70, 47.60, 42.47, 31.92, 29.69, 26.87, 23.33, 20.84, 20.58, 20.56, 17.24, 16.73.

HRMS(ESI) m/z calcd for C$_{58}$H$_{69}$N$_7$NaO$_{18}$[M+Na]$^+$ 1206.4998.

Compound 23: the compound 22 (22 mg) is dissolved in methanol (5 ml), and sodium methoxide (10 mg) is added. A reaction liquid is stirred at the room temperature for 2 h, the complete reaction of raw materials is detected by the TLC, and the reaction liquid is neutralized to about 7 by hydrogen-type Amberlite IR 120 resin. The resin is filtered, and the reaction liquid is purified by the silicagel column (dichloromethane/methanol, 10:1) after concentrating to obtain the compound 23 (18 mg). $[\alpha]_D^{20}$=−16.3°. $^1$H NMR (400 MHz, Chloroform-d) δ 7.60-7.13 (m, 20H), 7.12 (d, J=7.3 Hz, 1H, NHAc—H), 6.69 (d, J=9.8 Hz, 1H, NHAc—H), 5.23 (d, J=12.6 Hz, 1H, Cbz-H), 5.15 (d, J=12.4 Hz, 1H, Bn-H), 5.05 (d, J=12.3 Hz, 1H, Cbz-H), 4.96-4.83 (m, 2H, 1'-H, Bn-H), 4.79 (d, J=15.7 Hz, 1H, Bn-H), 4.72 (d, J=12.2 Hz, 1H, Bn-H), 4.66-4.49 (m, 2H, Bn-H, 2'-H), 4.36 (s, 1H, OH—H), 4.28 (d, J=9.5 Hz, 1H, 2A-H), 4.22 (d, J=16.0 Hz, 1H, Bn-H), 4.03 (d, J=7.3 Hz, 2H,1"-H, NCH$_2$—H), 4.00-3.84 (m, 4H, 3'-H, 1-H, 6"-H, OCH$_2$—H), 3.72 (dd, J=12.5, 6.1 Hz, 1H, 6"-H), 3.64 (q, J=6.7 Hz, 1H, 5-H), 3.42 (ddd, J=26.0, 12.9, 5.7 Hz, 4H, 5-H, 2"-H,3"-H, 4"-C), 3.33 (d, J=4.6 Hz, 1H, 3-H), 3.31-3.19 (m, 2H, 4'-H, 5"-C), 3.15 (td, J=9.7, 4.0 Hz, 1H, OCH$_2$—H), 2.88-2.74 (m, 2H, NH$_2$—H), 2.09 (s, 3 H, NHAc-Me), 1.96 (s, 3H, NHAc-Me), 1.72-1.57 (m, 2H, linker-CH$_2$), 1.32 (s, J=6.4, 3H, 6-Me), 1.03 (s, J=6.3, 3H, 6-Me). $^{13}$C NMR (101 MHz, CDCl3) δ 172.97, 172.65, 156.77, 138.85, 138.64, 137.11, 136.82, 128.75, 128.60, 128.38, 128.14, 128.05, 127.64, 127.50, 127.34, 127.26, 127.07, 101.41, 99.87, 82.13, 79.54, 77.36, 77.04, 76.72, 76.31, 75.31, 74.62, 74.34, 74.14, 72.82, 71.70, 70.92, 67.67, 67.56, 65.55, 62.61, 52.00, 49.50, 48.11, 42.01, 29.72, 26.65, 23.53, 17.50, 16.75. HRMS(ESI) m/z calcd for C$_{62}$H$_{77}$N$_3$NaO$_{20}$ [M+Na]$^+$ 1038.4570, found 1038.4538.

Compound 24: the compound 23 (12 mg) is dissolved in a mixed solvent of methanol (3 ml), dichloromethane (1 ml) and water (1 ml), two drops of glacial acetic acid are added, and then palladium carbon (10 mg) is added. A reaction is conducted in a BLT-2000 medium-pressure hydrogenator with hydrogen pressure of 0.4 MPa and reaction time of 12 h. After the reaction, a reaction liquid is filtered by diatomite and purified by CHROMAFIX C$_{18}$ec after concentrating to obtain the compound 24 (7 mg). $^1$H NMR (400 MHz, Deuterium Oxide) δ 5.03 (s, 1H, 1'-H), 4.51 (d, J=7.9 Hz, 1H, 1"-H), 4.37 (d, J=8.4 Hz, 1H, 1-H), 4.17 (s, 1H, 2'-H), 4.07 (q, J=6.6 Hz, 1H, 5'-H), 4.02 (s, 1H, 3'-H), 3.99-3.86 (m, 4H, 2-H, 4'-H, 6"-H OCH2-H), 3.80-3.75 (m, 1H, 5-H), 3.67 (ddt, J=16.6, 10.9, 6.0 Hz, 3H, 3-H, 6"-H, OCH2-H), 3.46 (m, 2H, 3"-H, 5"-H), 3.34 (t, J=9.3 Hz, 1H, 4"-H), 3.26 (t, J=8.6 Hz, 1H, 2"-H), 3.05 (t, J=6.9 Hz, 2H, NCH$_2$—H), 2.00 (s, 3H, NHAc-Me), 1.98 (s, 3H, NHAc-Me), 1.91 (t, J=6.4 Hz, 2H, CH$_2$—H), 1.23 (d, J=6.9 Hz, 3H, 6-Me), 1.21 (d, J=6.8 Hz, 3H, 6'-Me). $^{13}$C NMR (101 MHz, Deuterium Oxide) δ 174.35, 101.49, 100.22, 98.89, 76.54, 76.00, 75.46, 74.78, 72.81, 71.31, 70.63, 70.33, 69.63, 69.60, 68.39, 67.88, 66.88, 60.84, 51.31, 47.88, 37.60, 26.64, 22.20, 22.17, 15.39, 15.29. HRMS(ESI) m/z calcd for C$_{25}$H$_{45}$N$_3$NaO$_{14}$ [M+Na]$^+$ 634.2794, found 634.2789.

Example 7: Study on Effect of Solvent on Construction of Cis-Glycosidic Bond in Trisaccharide 24

It has become a relatively mature method in saccharide chemistry to use a neighboring group assisted by C-2 acyl of a saccharide ring to efficiently construct the 1,2-trans glycosidic bonds, while the 2-position acetyl, as the most easily available and the most effective protective agent in saccharide chemistry protection strategies, is generally given priority, such as the synthesis of the compound 18 in the disclosure. However, there is no mature method for 1,2-cis reaction. Referring to Example 6, other conditions remain unchanged, the solvent composition is changed, and the product configuration results are shown in Table 1.

TABLE 1

Results of different solvents constructing glycosidic bonds

| Solvent | Anhydrous dichloromethane (3.0 ml) | Anhydrous dichloromethane/ ether (1.5 ml + 1.5 ml) | Anhydrous dicloromethane/ ether/thiophene (1 ml + 1 ml + 1 ml) |
|---|---|---|---|
| Product | α/β = 1.2:1 | α/β = 6:1 | 100% α configuration |

It can be seen from Table 1 that the construction of the 1,2-cis-glycosidic bonds is greatly affected by solvents, among them, the mixed solvent of anhydrous dichloromethane/ether/thiophene has the best effect and can achieve a product with an even configuration, and the stereoselectivity of the reaction can be up to 100%.

Example 8: Effect of Acetyl Assembly Time on Carbohydrate Chain Synthesis

Figure 8:
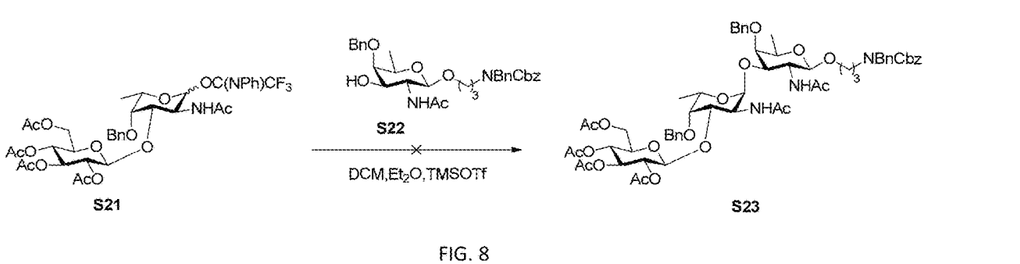
FIG. 8: a design drawing of a synthetic route of a trisaccharide S23.

Acetamido is assembled at a monosaccharide stage respectively to obtain an acetamido disaccharide donor S21 and an acetamido receptor S22. In this way, the synthesis of the target trisaccharide S23, which is not successfully completed by the glycosylation reaction, is conducted, the reason is that the acetamido at position 2 at the reducing end of the donor disaccharide is activated to form a stable exazoline ring intermediate, which limits the glycosidization reaction. The above results show that taking the non-participating azido as the precursor of acetamido will be conducive to improve the reactivity and stereoselectivity of target oligosaccharide synthesis.

What is claimed is:

1. A method of synthesizing an O-antigen trisaccharide of a *Pseudomonas aeruginosa* serotype O11, comprising:
    (a) synthesizing a D-glucose building block of formula II,
    (b) synthesizing an L-fucosamine building block of formula III,
    (c) synthesizing a D-fucosamine building block of formula IV by:
        (i) reacting 3,4,6-tri-O-acetyl-D-glucal with azidotrimethylsilane (TMS-$N_3$) and diphenyl disenenide ($Ph_2Se_2$) with iodobenzene diacetate (PhI(OAc)$_2$) to obtain 1-selenophenyl-2 azido glucose,
        (ii) removing acetyl under alkaline conditions, and
        (iii) methylating 6-C by incubation with 4-toluenesulfonyl chloride, to obtain D-fucosamine,
    (d) synthesizing a disaccharide fragment by attaching the D-glucose building block to the L-fucosamine building block, wherein a chemical structural formula of the disaccharide fragment is as shown in formula V:

formula V and
(e) linking together the disaccharide fragment and the D-fucosamine building block;
wherein:
the D-glucose building block or the L-fucosamine building block is linked with the D-fucosamine building block through a 1,2-α-cis-glycosidic bond,
the D-glucose building block is linked with the L-fucosamine building block through a 1,2-α-trans-glycosidic bond, and
construction of the 1,2-α-cis-glycosidic bond is conducted in a mixed solvent; and
the mixed solvent comprises two or more of dichloromethane, diethyl ether, and thiophene,
formula II, formula III, and formula IV have the following structures:

formula II formula III formula IV the linker comprises —$(CH_2)_n$—N—$Y_1Y_2$, or O—$(CH_2)_n$—$SY_1(Y_2)$, or O—$(CH_2)_n$—$N_3$, where:
n=1 to 10;
$Y_1$ is hydrogen (H) or benzyl (Bn);
$Y_2$ is hydrogen (H) or benzyl methoxycarbonyl (Cbz);
$R_1$ comprises hydrogen (H), an ester group, acetyl (Ac), benzoyl (Bz), pivaloyl (Piv), chloracetyl (ClAc), levulinyl (Lev) and allyl carbonyl (Alloc);
$R_2$, $R_3$, and $R_4$ are hydrogen (H) or an ester group and an ether group, and comprise acetyl (Ac), benzoyl (Bz), pivaloyl (Piv), chloracetyl (ClAc), levulinyl (Lev), allyl carbonyl (Alloc), benzyl (Bn), p-methoxybenzyl (pMBn), allyl (All), triphenylmethyl (Tr), monomethoxy triphenyl methyl (Mmt) and a silyl ether group;

$R_5$ and $R_6$ comprise hydrogen (H), an ether group, benzyl (Bn), p-methoxybenzyl (pMBn), allyl (All), triphenylmethyl (Tr), monomethoxy triphenyl methyl (Mmt) and a silyl ether group; and $R_7$, $R_8$, $R_9$, and $R_{10}$ comprise hydrogen (H), nitrogen (N) or acetyl (Ac).

2. The method according to claim 1, further comprising synthesizing a trisaccharide fragment by attaching the disaccharide fragment to the D-fucosamine building block, wherein a chemical structural formula of the trisaccharide fragment is as shown in formula I, wherein R is —$(CH_2)_n$—$NH_2$, or O—$(CH_2)_n$—SH; and n=1 to 10:

formula I

3. The method according to claim 1, further comprising pre-synthesizing a precursor of the O-antigen trisaccharide comprising variable group R, and obtaining the O-antigen trisaccharide by reduction, wherein a chemical structural formula of the precursor of the O-antigen trisaccharide is as shown in formula VI, formula VI wherein R is —$(CH_2)_n$—$NH_2$, or O—$(CH_2)_n$—SH; and wherein n is 1 to 10.

4. The method of claim 1, wherein the *P. aeruginosa* serotype O11 has a structure of: [-3)-α-L-N-acetylfucosamine-(1-3)-β-D-N-acetylfucosamine-(1-2)-β-D-glucose-(1-], which is a long-chain antigen formed by linking trisaccharide repeat fragments end-by-end.

* * * * *